US010214499B2

(12) United States Patent
Buekenhoudt et al.

(10) Patent No.: US 10,214,499 B2
(45) Date of Patent: Feb. 26, 2019

(54) DILUTE CHEMICAL REACTION PROCESS WITH MEMBRANE SEPARATION STEP

(71) Applicant: VLAAMSE INSTELLING VOOR TECHNOLOGISCH ONDERZOEK (VITO), Mol (BE)

(72) Inventors: Anita Buekenhoudt, Geel (BE); Pieter Vandezande, Herentals (BE); Dominic Ormerod, Hoogstraten (BE)

(73) Assignee: VLAAMSE INSTELLING VOOR TECHNOLOGISCH ONDERZOEK (VITO) (BE)

( * ) Notice: Subject to any disclaimer, the term of this patent is extended or adjusted under 35 U.S.C. 154(b) by 824 days.

(21) Appl. No.: 14/388,111

(22) PCT Filed: Apr. 19, 2013

(86) PCT No.: PCT/EP2013/058176
§ 371 (c)(1),
(2) Date: Sep. 25, 2014

(87) PCT Pub. No.: WO2013/156600
PCT Pub. Date: Oct. 24, 2013

(65) Prior Publication Data
US 2015/0050706 A1 Feb. 19, 2015

(30) Foreign Application Priority Data
Apr. 20, 2012 (EP) .................................... 12165047

(51) Int. Cl.
*C07D 267/00* (2006.01)
*B01D 61/02* (2006.01)
*B01D 61/12* (2006.01)
*B01D 61/14* (2006.01)
*C07C 67/343* (2006.01)
*C12P 13/02* (2006.01)

(52) U.S. Cl.
CPC .......... *C07D 267/00* (2013.01); *B01D 61/022* (2013.01); *B01D 61/025* (2013.01); *B01D 61/027* (2013.01); *B01D 61/12* (2013.01); *B01D 61/142* (2013.01); *B01D 61/145* (2013.01); *B01D 61/147* (2013.01); *C07C 67/343* (2013.01); *C12P 13/02* (2013.01); *B01D 2311/263* (2013.01); *B01D 2315/16* (2013.01); *Y02P 20/582* (2015.11)

(58) Field of Classification Search
CPC .............. B01D 67/0006; B01D 61/027; B01D 61/145; B01D 15/34; B01D 2311/04; B01D 61/147; B01D 61/025; B01D 2319/025; B01D 61/02; B01D 61/08; B01J 31/4061; B01J 8/006
See application file for complete search history.

(56) References Cited

U.S. PATENT DOCUMENTS

| 5,009,789 A * | 4/1991 | Helmer ................ B01D 61/145 210/195.2 |
| 5,859,159 A | 1/1999 | Rossi et al. |
| 5,962,625 A | 10/1999 | Yau |
| 6,254,779 B1 | 7/2001 | Jeffery et al. |
| 2004/0211729 A1* | 10/2004 | Sunkara ............... B01D 61/025 210/651 |
| 2004/0220416 A1 | 11/2004 | Jeffery et al. |
| 2013/0266991 A1 | 10/2013 | Kanamori et al. |

FOREIGN PATENT DOCUMENTS

| DE | 102005046250 A1 | 3/2007 |
| EP | 0160140 A2 | 11/1985 |
| WO | 2012/077697 A1 | 6/2012 |

OTHER PUBLICATIONS

Crossflow. Reverse osmosis basics & general information. Water Treatment Guide. 2009;1-2.*
Darvishmanesh et al. Performance of solvent resistant nanofiltration membranes for purification of residual solvent in the pharmaceutical industry: experiments and simulation. Green Chem. 2011;13:3476-3483.*
International Preliminary Report on Patentability for International Application No. PCT/EP2013/058176, dated Jul. 3, 2014 (8 pages).
International Search Report and Written Opinion of the International Searching Authority for International Application No. PCT/EP2013/058176, dated Jul. 3, 2014 (6 pages).
Written Opinion of the International Search Authority, PCT/EP2013/058176, dated Apr. 25, 2014 (14 pages).

* cited by examiner

*Primary Examiner* — Lynn Y Fan
(74) *Attorney, Agent, or Firm* — Lathrop Gage LLP; James H. Velema, Esq.

(57) ABSTRACT

Disclosed is a process for carrying out a cyclization reaction, a polymerization reaction, an enzymatic reaction showing substrate inhibition, an enzymatic reaction showing product inhibition, a reaction showing precipitation of the substrate or of a reactant, the process comprising the steps of
a) diluting a fresh substrate with solvent to form a diluted substrate-solvent mixture, and supplying this mixture to a reactor,
b) causing the reaction medium in the reactor to react,
c) discharging reaction mixture comprising reaction product, solvent, and substrate that has not reacted, to a first filtration membrane which is permeable to the solvent and impermeable to the substrate and to the catalyst or at least one of the reactants,
d) returning solvent from the permeate side of the first membrane to dilute the fresh substrate, and
e) returning retentate comprising substrate which has not reacted, from the first filtration membrane to the reactor.

20 Claims, 2 Drawing Sheets

DILUTE CHEMICAL REACTION PROCESS WITH MEMBRANE SEPARATION STEP

This application is a 371 filing of International Application No. PCT/EP2013/058176, filed Apr. 19, 2013, which claims priority to European Patent Application No. 12165047.7, filed Apr. 20, 2012. The entire contents of these applications are incorporated herein by reference in their entirety.

FIELD OF THE INVENTION

The present invention relates to an improved process for carrying out a chemical reaction which requires for at least one reason the reaction of a substrate in diluted form, the reaction being a cyclisation reaction, a polymerization reaction, an enzymatic reaction showing substrate inhibition, or a reaction showing precipitation of the substrate or of the reactant.

The process according to the present invention also relates to using a diluting substrate feed system and to a method for supplying substrate to a reaction medium.

BACKGROUND OF THE INVENTION

Reacting systems and substrate diluting system of the type described above are in particular intended for use with chemical reactions that are to be carried out with high dilution of the substrate, with concomitant avoidance of low product yield and use of large amounts of solvent.

Industry is often faced with the problem that certain reactions must be carried out at low concentration and/or high dilution of one or more of the substrates. In one example of a category of reactions high substrate dilution should minimize the risk for the formation of unwanted impurities. This is for instance the case in cyclisation reactions, in particular intramolecular macrocyclisation reactions, used in the production of active pharmaceutical ingredients. Indeed, too high substrate concentrations in this type of reactions favour intermolecular reactions and lead to polymerisation of the substrate in the reaction medium or to the occurrence of other unwanted side-reactions, thereby seriously decreasing the yield to the desired product and the product purity. To keep the selectivity up towards the desired end product and also the purity of the end product high, the reaction is usually carried out with high dilution of the substrate. High substrate dilution however involves the use of large amounts of solvent. Where batch reactions are employed, frequently used solvent dilution rates for this type of reactions mount to 100-1000 l/mole of substrate to permit keeping substrate concentration sufficiently low. In other words, for the production of small quantities of an end product, often the use of large volumes of solvent and the use of large reactor volumes is required. This entails serious constraints to the industry. Similar unwanted intermolecular side-reactions have been observed in certain types of polymerization reactions e.g. in the synthesis of cyclic polymers. These reactions clearly also benefit from high dilution. Enzymatic reactions with substrate inhibition exemplify another type of reactions that are preferably carried out at high dilution of the substrate, as a too high substrate concentration often leads to declining catalytic activity of the enzyme. In other types of reactions, low concentration of the substrate or other reactants is necessary to avoid unwanted precipitation, which typically occurs at higher concentrations.

Clearly, the processes performing such reactions as known in the art require a high dilution of the substrate and/or of one or more of the reactants in a reaction medium, and hence inherently necessitate the use of large volumes of solvent and therewith the use of large volume reactors, to produce small quantities of an end product only, with small reaction product yields per unit volume of reactor.

US 2004/0220416 A1 discloses a so-called "fed-batch" process for the singlet oxygen oxidation of organic substrates during which water is selectively removed from the reaction mixture by means of a membrane. The organic substrate, which must be either soluble in water or in an organic solvent miscible with water, is initially introduced into a reactor together with the solvent and the catalyst. Into the reactor is then introduced 2-90% strength $H_2O_2$, slowly or in portions. Water is introduced together with the $H_2O_2$, and is also formed during the catalysed disproportionation of $H_2O_2$. Via a pump, the reaction mixture is passed into a membrane unit, where the catalyst, the unreacted substrate and the product already formed are retained in the retentate and immediately reintroduced into the reactor. Water is separated off as permeate through the membrane. Optionally present water-miscible organic solvent may simultaneously also be separated from the reaction mixture, whereupon distillative separation of the water from the organic solvent takes place, the water is discarded and the organic solvent is reintroduced into the reactor. The process of US 2004/0220416 A1 is a so-called "fed-batch" process, from which water, formed in the reaction and also coming in together with the $H_2O_2$ reactant, needs to be removed in order to avoid that the reaction mixture becomes increasingly diluted by the water. As a result, losses in yield and in the efficiency of the singlet oxygen $^1O_2$ are prevented, as well as negative influences on the solubility, such as demixing. The purpose of the process of US 2004/0220416 A1 is to avoid dilution of the substrate, which is the opposite of the problem which is addressed by the present invention.

As a solution to the problem outlined above, related to improving the efficiency in performing chemical reactions under high dilution, it has been proposed to apply pseudo high dilution reaction conditions (K. Ziegler in "Methoden der Organischen Chemie" (Houben-Weil) vol 4/2, E. Müller, Ed. Georg Thieme Verlag, Stuttgart, 1955). "Simulated high dilution conditions" involves that a highly diluted solution of the substrate concerned is added at a slow supply rate to the reactor, which contains a relatively high concentration of the other reactants. In some cases, this method permits reducing solvent dilution rates used to typically 10-100 l/mol of substrate. However, when compared to dilutions used in conventional reactions which typically vary from 0.5-5 l/mol, this method still involves the use of relatively large solvent volumes, and the limited reactor capacity associated therewith still necessitates using large reactor volumes for low productivity and small product yields. Moreover, the simulated high dilution method, tends to be efficient only for those reactions in which the kinetic product is formed, and does not work for reactions that are reversible to any significant degree.

There is thus a need for a device and a method which are particularly suitable for use with reactions which have to be carried out at low concentration of one or more of the substrates. In particular there is a need for a device and a method which permits to perform reactions which are to be carried out in high dilution in reactors with a reduced volume, using reduced quantities of solvent, while providing a sufficiently high reaction yield and good selectivity to the desired reaction product. The present invention provides an answer to these needs.

SUMMARY OF THE INVENTION

This problem is solved according to the present invention with a process as defined by the first claim.

In an embodiment, the invention provides a process for carrying out a chemical reaction of a substrate (X) in a diluted reaction mixture comprising a solvent (S), the reaction being selected from a cyclisation reaction, a polymerization reaction, an enzymatic reaction showing substrate inhibition, an enzymatic reaction showing product inhibition, a reaction showing precipitation of the substrate or of the reactant, and combinations thereof, the process comprising the steps of
a) diluting the substrate with solvent in a diluting substrate feed system to form a diluted substrate-solvent mixture, and supplying the diluted substrate-solvent mixture to the inlet of a reactor,
b) causing the reaction medium in the reactor to react,
c) discharging from an outlet of the reactor the reaction mixture comprising reaction product, solvent, and substrate that has not reacted,
d) conducting the reaction mixture to a first membrane with a retentate side and a permeate side, whereby the first membrane is permeable to the solvent (S) and provided to be impermeable to the substrate (X) and to at least one of the group consisting of the catalyst, the reactants which are caused to react with the substrate and combinations thereof,
e) returning solvent (S) which permeated the first membrane from the permeate side of the first membrane to the diluting substrate feed system to dilute the substrate in the diluting substrate feed system, and
f) returning retentate (R) comprising substrate (X) that has not reacted, from the retentate side of the first membrane to the reactor.

Thereto, the device used in the process of this invention is characterized in that the reactor outlet is coupled to a first membrane or filtration membrane with a retentate side and a permeate side, in that the said first membrane is permeable to the solvent and provided to be impermeable to the substrate, in that the permeate side of the said first membrane is connected to the diluting substrate feed system to return solvent which permeated the said first membrane to the diluting substrate feed system to provide dilution of the substrate in the diluting substrate feed system, and in that the retentate side of the said first membrane is connected to the reactor to return retentate comprising substrate that has not reacted, to the reactor.

The present invention therewith makes use of a device which comprises
- a diluting substrate feed system by which a substrate-solvent mixture with a low substrate concentration may be supplied to the reactor, starting from a feed solution having a high substrate concentration in solvent and,
- a membrane or filtration membrane which is coupled to the reactor outlet to permit continuous, in-situ solvent recuperation and recycling of the solvent within the device.

The diluting substrate feed system enables the controlled supply of a substrate-solvent mixture having a low substrate concentration, fairly independently of what the substrate concentration is in the feed solution, which may be significantly higher. Because the high substrate dilution is only applied to the substrate volume which is actually supplied to the reactor, reactions which require high dilution of one or more to the substrates or reactants may be carried out using substantially reduced quantities of solvent, while relatively high reaction yields may be achieved, even in reactors having a relatively small volume. Thus, the present invention permits reducing the volume of solvent used in the process to 0.5-25 l/mol of substrate, while product yields achieved are typically as high as those achieved with reactions carried out at high dilution in large reaction volumes of 100-1000 l/mole of substrate. Typically the product yield is determined by the substrate concentration at the reactor inlet, and is at least equal to the yield obtained in a standard batch reaction performed at the same low concentration.

DETAILED DESCRIPTION

Figure 1:
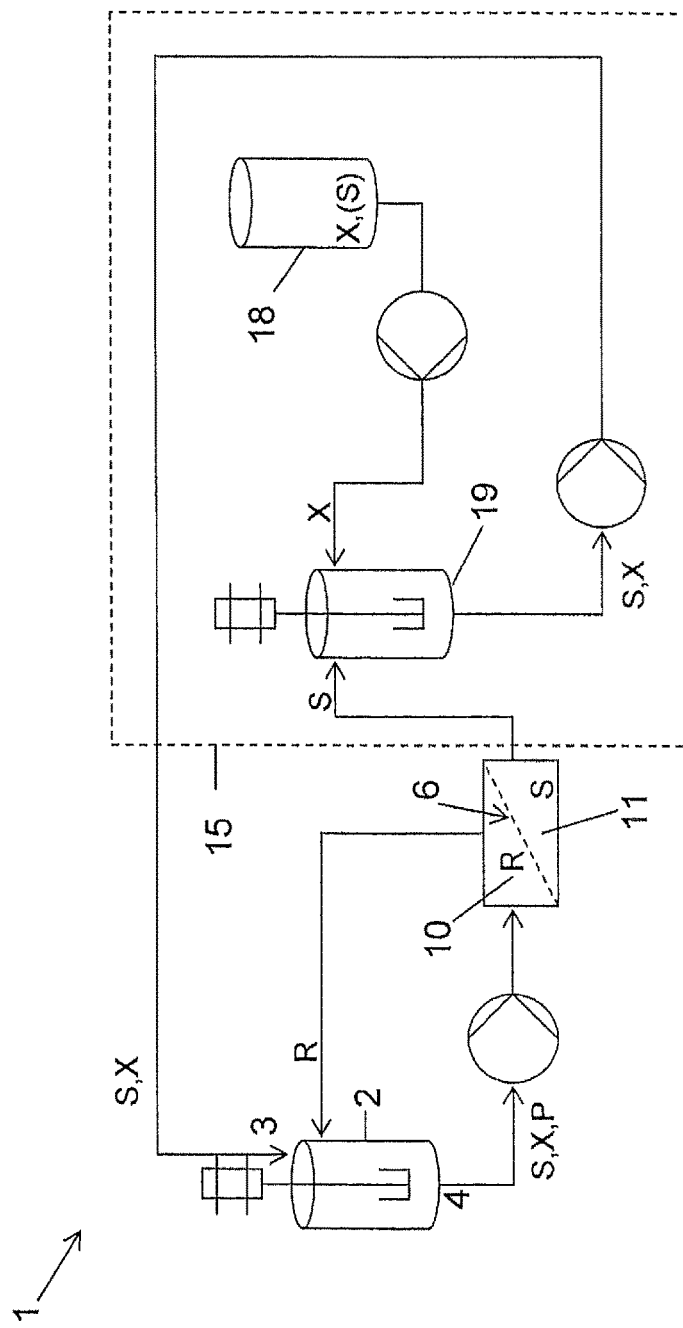
FIG. 1 shows a schematic view of a first preferred embodiment of the invention, wherein the device comprises a diluting substrate feed system based on a mixing tank with a high solvent-substrate ratio.

The present invention will be described in the following with respect to particular embodiments and with reference to certain drawings but the invention is not limited thereto but only by the claims. Any drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. Accordingly, the terms "comprising" and "including" encompass the more restrictive terms "consisting essentially of" and "consisting of".

In the context of the present invention, the terms "membrane" and "filtration membrane" are used interchangeably.

In the context of the present invention, the substrate is preferably a compound which is able to react in an intra- and/or an intermolecular pathway. An intramolecular chemical reaction is a reaction of a particular molecule with itself, such as in a cyclisation reaction. An intermolecular reaction is a reaction of a molecule with another molecule. An intermolecular reaction may be a homo-intermolecular reaction, whereby the two molecules are of the same chemical compound. An intermolecular reaction may also be a hetero-intermolecular reaction, whereby the two molecules are of a different kind or chemical compound. The present invention is primarily concerned with such reactions and may have as a target to reduce the occurrence or even avoid one of those reactions in favour of a competing and desired reaction, and which may be favoured by carrying out the reaction in conditions of high dilution of the substrate.

In an embodiment, the substrate is an organic compound, meaning that the molecule contains a number of atoms which are covalently bound to each other. In an embodiment, the molecule of the organic substrate contains a number of carbon and hydrogen atoms, yet other atoms, conveniently called "hetero atoms", such as oxygen, nitrogen, sulphur, may also be present. The organic compound may also have an ionic part, and may for instance be present as a salt.

The process according to the present invention is preferably operated with ongoing feed of fresh substrate to the reactor, preferably such that the amount of substrate present in the reactor is replenished as it is consumed. The process may thus comprise a "fed-batch" operation in which the substrate is fed slowly or intermittently over time in one or more portions to a reactor containing the other ingredients required for carrying out the reaction. The fresh substrate may also be fed continuously to the reactor. The present invention is also concerned with diluting the substrate, with solvent, before the substrate may become exposed to conditions under which it may react.

In the process according to the present intention, optionally reaction product may be removed from the reactor, preferably selectively. The removal of reaction product may be performed continuously, or with intervals and in portions.

In the context of the present invention, cyclisation reactions are chemical reactions whereby at least one ring is formed. A ring may be formed by one part of a molecule chemically condensing with another part of the same molecule, in which case the reaction is an intramolecular cyclisation reaction. A ring may also be formed by a first part of a first molecule chemically connecting to or condensing with a first part of a second molecule, followed by a second part of the second molecule connecting to or condensing with a second part of the first molecule, in which case the reaction is an intermolecular cyclisation reaction. In such intermolecular cyclisation reaction, there may also be three or more molecules which form one single ring.

The first filtration membrane present in the device of the process of the present invention, is used to separate or isolate the solvent from the reaction product and where desired from other components contained in the reaction mixture. The thus isolated solvent may continuously be recycled within the system, between the diluting substrate feed system and the reactor, thereby minimizing solvent consumption and waste. The solvent contained in the permeate returned from the reactor to the diluting substrate feed system, replenishes solvent which is supplied from the diluting substrate feed system to the reactor, and assists in achieving the envisaged substrate dilution in the substrate supply to the reactor. On completion of the reaction, the solution containing products may be removed and subjected to classical isolation procedures or, depending on the constraints of the following synthetic steps, used directly in the following reaction. The use of membrane assisted solvent recovery thereby permits recycling of the solvent within the device and process, and minimizing the amount of solvent used, while permitting substrate supply at the desired substrate concentration. Furthermore, it provides the possibility of performing chemical reactions under liquid-liquid processing conditions, which in turn implies contained production, resulting in lower operator exposure to chemical entities and compounds which may be biologically active, and a reduction in process operations. By recycling of the solvent with a membrane within the process, the present invention permits overcoming the problems associated with the conventional solvent recovery techniques and realizing significant process economies as explained below.

By using a filtration membrane for the solvent recovery within the system, energy consumption otherwise needed to recover the solvent may be kept low. Indeed, the known and conventional techniques used to recover solvents and/or to separate a solvent from the reaction products or substrate or reactants, are often energy consuming, as is the case for e.g. distillation, evaporation and crystallization. Moreover, solvent recovery efficiency is typically rather low with the conventional techniques (only 50-80%), addition of extra chemicals as entrainers is sometimes required, and in many cases these operations are unsuitable for use with the reaction involved or the reaction conditions used. As a consequence, these traditional solvent recovery operations are not suitable for direct coupling to a reactor, and may not provide continuous in-process solvent recovery, as is the case with the present invention. Furthermore by using a membrane, solvent recovery from the reaction mixture may be carried out at mild temperatures. This may be of special importance in case of heat sensitive compounds, for example pharmaceutical active ingredients and functional food ingredients, in order to minimize the risk that they would loose their activity, their texture and/or their colour or would undergo thermal degradation.

As such, the present invention assists the chemical industry in its efforts towards more sustainability. To exemplify the above, reference is made to the pharmaceutical industry which is committed to bringing key medicines to the patient with minimal environmental impact. In recent years, significant efforts have been invested to improve efficiency, to reduce waste, and to enhance quality and control in pharmaceutical research and development, and manufacturing. This effort is driven by the desire not only to reduce costs but also to increase the sustainability of the manufacturing process. Optimization of resource use is one of the aims of sustainability and green chemistry. This challenge has resulted in the adoption of Process Mass Intensity (PMI) as the preferred metric aimed at driving greater efficiencies in pharmaceutical syntheses. An explanation as to why this metric has been chosen is given by Jimenez-Gonzalez et. al in Org. Process Res. Dev., 15 (2011) 912-917. PMI is defined as the total mass of materials used to produce a specified mass of product. Materials include reactants, reagents, solvents used for reaction and purification, and catalysts. Ideally this total equals unity when no waste is produced and all materials are incorporated into the product. In reality, PMI values in pharmaceutical industry are typically 25 to 100. The present invention, in providing a solution for high dilution reactions which permits the use of significantly lower amounts of solvent in combination with an acceptable product yield, allows the reduction of the PMI values of this type of reactions, to the typical envisaged values.

A recent article published by Sereewatthanawut et. al. in Org. Process Res. Dev 14 (2010) 600-611 discloses the use of membrane technology for solvent purification, in which the organic solvent was purified and recycled using a solvent resistant nanofiltration membrane. The solvent purification is conceived as a post reaction process which takes place entirely independently of the reaction. The article does not disclose to use a membrane for in-situ solvent recuperation, nor does it disclose to use this feature to achieve a controlled feed of substrate to the reactor.

In the state of the art, filtration membranes have predominantly been used in post reaction purification processes. Well known examples are Membrane Bioreactors (MBR) where ultrafiltration membranes are coupled to a sludge bioreactor in order to filter out and produce purified water. Other examples using solvent resistant nanofiltration membranes may be found within the literature, a comprehensive overview of which is presented in the review article by Vankelecom et. al. in Chem. Soc. Rev., 37 (2008) 365-405.

Examples where solvent-stable membranes are connected to and play a role within a reactor system are far fewer and amongst these, those used in biotransformations using biocatalysts in so called "membrane bioreactors" or MBRzs, typified in the article by Valadez-Blanco et. al. in J. Membr. Sci. 317 (2008) 50-64 are predominant. Membrane bioreactors or MBRs for bio-transformations are used as an alternative for direct contact biphasic bioreactors. In these membrane bioreactors, a solvent resistant membrane separates the aqueous (biocatalyst) and organic (substrate and product) phases in the reactor. However, whereas these membrane bioreactors are advantageous over direct contact bioreactors for a number of reasons, they do suffer from the fact that they have 2 to 3 times lower volumetric productivity than the latter bioreactor. Other examples where a membrane is used as a barrier between two solvents include anti-solvent membrane crystallization, exemplified in the article by Di Profio et. al. published in J. Pharma Sci., 98 (2009) 4902-4913. Again crystallization occurs separately from the reaction and is used to control the crystal form the product is isolated in.

In Biochem. Eng. J. 12 (2002) 223-229 Gan discloses a method for enzymatic hydrolysis of crystalline and semi-crystalline cellulose by fungal cellulase in a reactor which integrates a reaction and separation zone inside one device separated by an ultrafiltration membrane. The ultrafiltration membrane allows the in-situ product separation from the reaction mixture. The reactor is complemented by continuous on-line feeding and in-situ electro-kinetic membrane cleaning to maintain separation and reactor efficiency. No solvent recuperation useful for the on-line feeding was described.

More recently some examples have been published whereby nanofiltration membranes play a role in a reactor set-up that is not a biotransformation. These include the articles by Janssen et al. published in Angew. Chem. Int. Ed. 49 (2010) 7738-7741 and So et al. in Org. Process Res. Dev. 14 (2010) 1313-1325, though it has to be noted that the latter is used to remove excess reagents and perform solvent exchange after the reaction is complete and thus is not really integral to the reactor or reaction process. The former study involves an in-situ separation of catalyst from reaction products in order to increase the catalysts turnover number.

Others have also used membranes to separate catalysts from reaction mixtures in order to recycle catalysts and thus effectively increase their turnover number, though not necessarily in-situ. Examples include articles by Laue et al. in Adv. Synth. Catal. 343 (2001) 711-720, and Nair et al. in Org. Process Res. Dev. 13 (2009) 863-869, both focusing on hydrogenation catalysts. Plenio et al. have demonstrated the recycling of palladium catalysts via membranes in Adv. Synth. Catal. 345 (2003) 333-336 and Organometallics 28 (2009) 3922-3927. Also Ronde et al. in ChemSusChem 2 (2009) 558-574 and Tsoukala et al. in ChemSusChem 5 (2012) 188-193 published the membrane based separation of palladium catalysts and products. Recycling of metathesis catalysts, in particular derivatives of the Grubbs and Hoveyda-Grubbs catalysts, have been demonstrated in a number of articles including those published by Keraani et al. in ChemSusChem 1 (2008) 927-933 and Catal. Today 156 (2010) 268-275, Schoeps et al. in Chem. Eur. J. 15 (2009) 2960-2965, and van der Gryp et al. in J. Membr. Sci. 353 (2010) 70-77. Other metal catalysts which have been recycled include an osmium dihydroxylation catalyst published by Branco et. al. in Adv. Synth. Catal. 350 (2008) 2086-2098 and a copper catalyst published by Cano-Odena et. al. in Chem. Eur. J. 16 (2010) 1061-1067.

In all of the literature examples discussed above, the role of the membrane is limited to its use solely as a separation member, i.e. for its separation function. None of the literature examples cited discloses that a membrane would be suitable for use in controlling a reaction, in particular the substrate supply thereto, and the reaction outcome, in particular yield and selectivity.

Within the framework of the present invention the first filtration membrane is selected such that it is impermeable to the substrate. With "impermeable" is meant that the first membrane preferably has a typical rejection of 80 to 100%, preferably more than 95% for the substrate. The first filtration membrane is further selected such that it is highly permeable to the solvent in order to guarantee adequate substrate dilution by the solvent in the diluting substrate feed system.

Preferably, the first filtration membrane is also impermeable to one or more of the reaction product, catalyst and one or more reactants which are caused to react with the substrate. Preferably the retentate side of the first filtration membrane is connected to the reactor to return one or more of these reaction species to the reactor. To permit optimal use of all components contained in the reaction mixture and minimize losses, the first membrane preferably has a typical rejection of 80 to 100%, preferably at least 95% for the reaction components, in particular for any reactants provided to react with the substrate, the reaction product or products and catalyst contained in the reaction mixture. The rejection of the first membrane for all these components may be the same or different. If so desired however, permeation of one or more of these components may be permitted and in that case a lower rejection of the component involved may be permitted.

Within the scope of this invention, the first filtration membrane may be made from a wide variety of materials and a wide variety of filtration membranes with varying cut-off values may be used. With cut-off or cut-off value is thereby meant the molecular mass of a molecule of which 90% is rejected by the membrane. The first membrane will be selected by the skilled person taking into account the nature of the solvent, substrate, or other reaction components the membrane is intended to reject. Depending on the nature of the reaction, substrate, reactants and solvent involved, the first membrane may be an ultrafiltration membrane with a typical cut-off ranging from 2 to 500 kDa, or a microfiltration membrane with a typical cut-off for molecular weights above 500 kDa as probably more suitable in the case of enzymatic reactions or polymerization reactions. For reactions involving smaller molecules, for example macrocyclization reactions, the membrane will more probably be a nanofiltration membrane with typical cut-off values ranging from 200 Da to 2 kDa or even a reverse osmosis membrane with a typical cut-off of below 200 Da.

In one embodiment of the invention, the diluting substrate feed system may comprise a conventional mixing system for mixing substrate and solvent. According to that embodiment the diluting substrate feed system comprises a substrate feed tank containing a concentrated substrate solution, which substrate feed tank is connected to a mixing tank to supply substrate to the mixing tank with the purpose of mixing the substrate in the mixing tank with an appropriate amount of solvent to obtain the appropriate dilution of the substrate to be supplied to the reactor for reaction therein.

According to another embodiment, the diluting substrate feed system for supplying substrate to the reactor may comprise a second filtration membrane which is permeable to the solvent, wherein the substrate rejection of the second filtration membrane should be such that the permeate of the second membrane has the desired substrate concentration, wherein the permeate side of the second filtration membrane is connected to the reactor for supplying the permeate with the desired concentration to the reactor. The second filtration membranes thus functions to control the permeation of substrate supplied to the reactor. By adjusting the substrate rejection by the second membrane, the concentration of substrate to the reactor may be controlled.

The second membrane dedicated to the low concentration addition of the substrate to the reactor, will usually be selected such that it is practically impermeable to the substrate, or in other words shows high to very high substrate rejections. Typical substrate rejection of the second membrane will usually vary from 50 to 99.5%, preferably from 60 to 95%. The second membrane will usually also have a high rejection for any other components contained in the mixture to be supplied to the reactor, such as any other reactants or catalyst and so on, but this is not mandatory. Depending on the reaction and the substrate or reactants involved, the appropriate second membrane may be a microfiltration, ultrafiltration, nanofiltration or reverse osmosis membrane.

In many cases, especially related to pharmaceutical manufacturing, the first and second filtration membrane are preferably nanofiltration membranes, more preferably solvent resistant nanofiltration membranes. Nanofiltration provides the possibility to isolate and/or separate molecules with similar physical properties on molecular scale, by simply applying a pressure gradient over a selective membrane. Separation is based on different molecular dimensions of the species to be separated and/or on different affinities with the membrane. Nanofiltration may often be directly carried out on the reaction medium, at any temperature, without addition of reactants, thereby minimising the risk to decomposition or auto-reaction of the molecule, and the risk to activity, colour or texture changes.

Within the framework of this invention, the first and the second membrane may be the same or different. Usually however they will be different, since the function of the first membrane is to reject one or more of the substrate, reactant, reaction product, catalyst and any other compounds contained in the reaction mixture except for the solvent, whereas the function of the second membrane is to permit permeation of a small, controlled amount of substrate, although the second membrane may function to reject one or more reactants to a desired extent as well.

Microfiltration, ultrafiltration, nanofiltration and reverse osmosis membranes and their use for filtration technology in aqueous medium are well-known in the art. A wide variety of membranes suitable for filtrations in aqueous medium is commercially available. When the filtration medium contains an organic solvent, as will often be the case in many reactions where the present invention may be used, it is advisable to select the membrane in such a way that it is chemically and thermally compatible with the reaction medium. Since the end of the 90's specific solvent resistant membranes appropriate for filtrations in different organic solvent media have become commercially available, especially in the nanofiltration range.

The first and second filtration membrane are preferably chosen such that the membrane rejection, cut-off and permeate flux meet the requirements imposed by the process and by the substrate, solvent and reaction product involved in the process. The first and second filtration membrane are preferably chosen such that they show a minimal risk to reacting with the components contained in the mixtures to which they are exposed, and to degradation of the components in the mixtures to which they are exposed, as well as a minimal risk to swelling as this may alter the flux through the membranes and their rejection properties. Thereby the membranes are preferably chosen such that they show a stability of several months to several years in contact with the selected reaction solvent.

Suitable materials for use as first and second filtration membrane in the device of this invention include polymeric or ceramic materials. Preferred materials include those polymeric materials suitable for fabricating microfiltration, ultrafiltration, nanofiltration or reverse osmosis membranes, including but not limited to polyethylene (PE), polypropylene (PP), polytetrafluoroethylene (PTFE), polyvinylidene difluoride (PVDF), polysulfone (PSf), polyethersulfone (PES), polyacrylonitrile (PAN), polyamide (PA), polyimide (PI), polyetherimide (PEI), polyamideimide (PAI), cellulose acetate (CA), polyaniline (PAn), polybenzimidazole (PBI), polyetheretherketone (PEEK), and combinations and mixtures thereof.

Specific examples of membrane materials suitable for use in the present invention include a composite material comprising a support and a thin selectively permeable top layer, wherein the latter may be formed from or comprises one or more polymers selected from but not limited to (modified) polysiloxane based elastomers, including polydimethylsiloxane (PDMS) based elastomers, ethylene-propylene-diene (EPDM) based elastomers, polynorbornene based elastomers, polyoctenamer based elastomers, polyurethane (PU) based elastomers, butadiene and nitrile butadiene rubber based elastomers, natural rubber and butyl rubber based elastomers, polychloroprene (Neoprene) based elastomers, epichlorohydrin elastomers, polyacrylate elastomers, polyvinylidene difluoride (PVDF) based elastomers, polyethylene, polypropylene, polytetrafluoroethylene (PTFE), polyamide, polyetherblock amides (PEBAX), poly(1-trimethylsilyl-1-propyne) (PTMSP) and other polyacetylenes, polyamide, polyaniline, polypyrrole, and combinations and mixtures thereof.

The polymeric membranes may be made by any technique known from the art, including phase-inversion, sintering, stretching, track etching, template leaching, interfacial polymerisation, solvent casting, dip-coating, spin-coating and spray-coating. Membranes may be cross-linked or otherwise treated so as to improve their stability in the reaction solvents.

Other specific examples of suitable membrane materials include those produced from inorganic materials, for example silicon carbide, silicon oxide, zirconium oxide, titanium oxide, zeolites, and combinations or mixtures thereof, prepared using any technique known to those skilled in the art, such as e.g. sintering, leaching, hydrothermal or sol-gel processing. The inorganic membranes provided by Inopor GmbH (Germany), covering the entire spectrum from microfiltration to nanofiltration, provide an example.

The membranes used in the present invention may also comprise a polymer membrane with dispersed organic or inorganic particles in the form of powdered solids (mixed matrix membranes). The powdered solids will usually be present at amounts up to 20 wt. % of the polymer membrane and include carbon molecular sieve particles, zeolites, metal oxides, such as titanium dioxide, zirconium oxide, zinc oxide and silicon dioxide. Examples are the materials available from Evonik Degussa AG (Germany) under their Aerosol and AdNano trademarks. Mixed metal oxides such as mixtures of cerium, zirconium, and magnesium oxides may also be used. Preferably the matrix particles have a number average diameter of less than 1.0 micron, more preferably less than 0.1 micron, and most preferably less than 0.01 micron.

These mixed-matrix membranes may be made by any technique known from the art, including sintering, stretching, track etching, template leaching, interfacial polymerisation or phase inversion. The polymers in the membranes may be cross-linked, or the membranes may otherwise be treated so as to improve their stability in the reaction solvents.

Examples of solvents suitable for use with the present invention include water, aromatics, alkanes, ketones, glycols, chlorinated solvents, esters, ethers, amines, nitriles, aldehydes, phenols, amides, carboxylic acids, alcohols, furans and dipolar aprotic solvents, and mixtures of two or more of the aforementioned solvents as well as mixtures of one or more of the aforementioned solvents with water. Specific examples of suitable solvents include toluene, xylene, benzene, styrene, anisole, chlorobenzene, dichlorobenzene, chloroform, dichloromethane, dichloroethane, methyl acetate, ethyl acetate, butyl acetate, methyl ether ketone (MEK), methyl isobutyl ketone (MIBK), acetone, ethylene glycols, ethanol, methanol, propanol, butanol, hexane, cyclohexane, dimethoxyethane, methyl-tertiary-butyl ether (MTBE), diethyl ether, adiponitrile, N,N-dimethyl formamide, dimethyl sulphoxide, N,N-dimethyl acetamide, dioxane, nitromethane, nitrobenzene, pyridine, carbon disulfide, tetrahydrofuran (THF), methyl-tetrahydrofuran, N-methyl pyrrolidone (NMP), N-ethyl pyrrolidone (NEP), acetonitrile, and mixtures of two or more of the aforementioned solvents as well as mixtures of one or more of the afore mentioned solvents with water.

Examples of reactions which may be advantageously carried out using the process of this invention include those where high dilution of one or more of the substrates in the reaction medium is required. Examples of such processes include macrocyclisation reactions, where with increasing chain length the probability of the chain termini approaching each other to cause cyclisation decreases because of the negative entropy change as the disordered open chain molecule is converted to the ring shaped transition state. With such reactions, cyclisation is favoured only at low substrate concentration whereas polymerisation becomes more favoured at higher substrate concentration. Examples of macrocyclisation reactions include macrolactamisation reactions, macrolactonisation reaction, metal catalysed macrocyclisations, reversible macrocyclisations, macrocyclisation via a hetero-molecular substitution-cyclisation sequence, etc. Active pharmaceutical ingredients (APIs) are often macrocyclic products. Typical substrate dilutions in these reactions vary from 100-1000 l of solvent per mole of substrate.

Similarly unwanted intermolecular side-reactions may occur in some polymerization reactions, e.g. in the synthesis of cyclic polymers. Also these reactions may clearly benefit from the present invention. Other reactions which require high dilution of the substrate are enzymatic reactions showing substrate inhibition. In this case a too high concentration of substrate may lead to a decline of the catalytic activity of the enzyme. In other reactions, low concentration of the substrate or of the reactants is required in order to avoid precipitation at high concentrations. In all these and similar cases, performing the reaction at high dilution is favourable, and the use of the present invention may lead to high yields in combination with low solvent use.

Examples of reactors suitable for use in the present invention may vary widely in nature and include conventional batch reactors as well as continuously stirred reactors, flow-reactors or micro-reactors. Suitable reactors also include the feed tank of a cross-flow membrane filtration unit or the stirred feed tank of a dead-end filtration unit.

The present invention also makes use of a diluting substrate feed system for producing a diluted substrate-solvent mixture with a desired substrate concentration from a concentrated substrate-solvent mixture, which is characterized in that the diluting substrate feed system comprises
  a substrate feed containing the substrate and the solvent in a first concentration ratio
  means for supplying the concentrated substrate/solvent mixture to
  a filtration membrane which is permeable to the substrate and the solvent, wherein the permeability of the membrane for the solvent is higher than the permeability of the membrane for the substrate (X) and is selected such that a permeate of the membrane contains the substrate in a desired concentration in the solvent.

As discussed above, the membrane preferably has a substrate rejection of 50%-99.5%, preferably 60%-95%.

The present invention also relates to a method for carrying out a chemical reaction, by causing a substrate to react in a diluted reaction mixture comprising a solvent.

The invention is now illustrated in detail in the figures shown in the accompanying drawings, with the figure description below.

FIG. 1 shows a schematic view of a first preferred embodiment of the invention, wherein the device comprises a diluting substrate feed system based on a mixing tank with a high solvent-substrate ratio.

Figure 2:
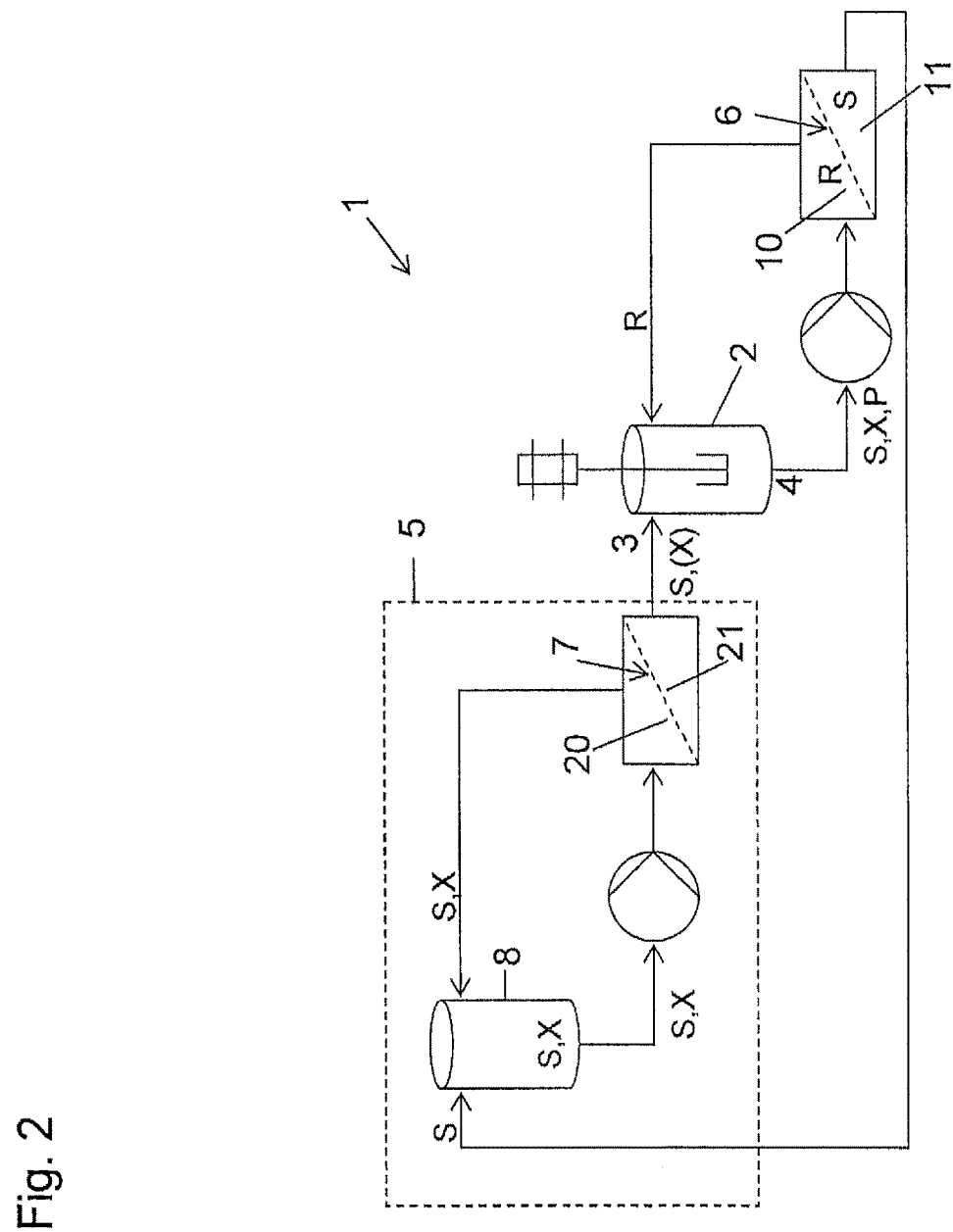
FIG. 2 shows a schematic view of a second preferred embodiment of the invention, wherein the device comprises a diluting substrate feed system comprising a second membrane with a high substrate rejection.

FIG. 2 shows a schematic view of a second preferred embodiment of the invention, wherein the device comprises a diluting substrate feed system comprising a second membrane with a high substrate rejection.

In the preferred embodiments shown in FIGS. 1 and 2, the device (1) used in the process of the present invention comprises a reactor (2) provided to contain a liquid reaction medium in which a substrate (X) contained in a solvent (S) is caused to react. The reactor (2) comprises an inlet (3) for supplying a solution of substrate (X) and solvent (S) to the reactor. The solution is preferably a homogeneous solution. Inlet 3 may also serve to supply reactants, catalyst and other reactive species to the reactor (2). The reactor (2) comprises an outlet (4) for discharging a liquid flow containing any substrate (X) that has not reacted from the reactor (2). The reactor outlet (4) may also serve to discharge reaction product (P), solvent (S) and any other products contained in the reaction mixture. The reactor outlet (4) is connected to a first membrane (6), with the purpose of conducting from the reactor (2) the solution containing solvent (S), product (P), un-reacted substrate (X) and possibly other species involved in the reaction to the first membrane (6). The first membrane (6) is preferably chosen such that it is highly permeable to the solvent (S), and has a high rejection rate for the substrate (X). This membrane will typically have a substrate (X) rejection of 80-100%, preferably at least 95%.

The first membrane (6) has a retentate side (10) and a permeate side (11). The permeate side (11) of the first membrane (6) is connected to a diluting substrate feed system (5, 15) to conduct permeate of the first membrane (6) to the diluting substrate feed system (5). The diluting substrate feed system (5, 15) is connected to the reactor (2) through the reactor inlet (3). This way, recycling of the permeate within the system is permitted and solvent (S) that has been fed from the reactor (2) to the first membrane (6) and has permeated the first membrane (6), is returned from the permeate side (11) of the first membrane (6) to the reactor (2), over diluting substrate feed system (5, 15). Thus a substrate/solvent mixture with a desired degree of dilution may be produced and fed to the reactor (2). The diluting substrate feed system (5, 15) is provided to permit supplying to the reactor (2) a substrate-solvent mixture with high dilution of the substrate (S) in comparison to the substrate feed (8,18), with the purpose of minimizing the risk on the formation of unwanted impurities. In other words, the diluting substrate feed system (5, 15) functions to dilute the substrate (X) to any desired extent before it is supplied to the reactor (2). The substrate/solvent ratio or the degree of dilution may vary within wide ranges, but preferably varies from 50-1000 L/mol at the reactor inlet (3).

To effectuate the liquid flows, pressure may be used as a driving force, as is conventionally applied in microfiltration, ultrafiltration, nanofiltration and reverse osmosis.

The retentate side (10) of the first membrane (6) is connected to the reactor (2) to recycle or return to the reactor (2) the components that have been rejected by the first membrane (6), in particular the substrate (X). This way, any substrate (X) which has not reacted may be circulated and recycled within the system, and substrate (X) which has reacted may be replenished through the diluting substrate feed system (5, 15). If so desired, the first membrane (6) may be chosen such that it rejects reaction product (P) and any catalyst and/or other reactants contained in the reaction mixture. These rejected reaction components are preferably also returned to the reactor (2). If so desired however, the retentate may be further processed to permit recovery of one or more compounds contained in the retentate, for example to isolate the reaction product (P) from the remainder of the rejected flow. The first membrane (6) may also be chosen such that it is permeable to one or more of the reaction product (P), catalyst and/or other reactants contained in the reaction mixture, for example to permit recovering of the reaction product (P). Thereby care should be taken to avoid that components contained in the permeate react with each other.

As may be understood from the description above, the membranes in the device of the present invention may also be operated in diafiltration mode. The latter involves a liquid filtration technique in which a feed liquid containing at least two compounds, i.c. the solvent and the substrate, is contacted with a membrane and pressurised to force a fraction of the liquid to pass through the membrane. The membrane has a higher rejection for the substrate, and a lower rejection for the solvent. During filtration, fresh solvent is supplemented to the feed side of the membrane to make up for the liquid permeating through the membrane, so as to be able to work at constant feed volume. The first membrane 6 may be operated in a dead-end filtration mode where the liquid permeating the membrane is supplied in a direction perpendicular to the membrane. The first membrane 6 is however preferably operated in a cross-flow filtration mode where the liquid permeating the membrane is supplied in a direction parallel to the membrane, as this ensures a sufficient degree of turbulence at the membrane surface.

As will be understood from the description above and below, the presence of a first membrane (6) which is coupled to the reactor (2) permits a continuous, in-situ solvent recuperation and recycling of the solvent (S) within the device, thereby minimizing solvent losses. Separation of solvent (S) from the reaction mixture permits the recycling of the solvent (S) within the system, and to mix recycled solvent (S) with the substrate (X) feed to achieve the envisaged dilution of the substrate (X), while minimising solvent consumption and waste.

According to a preferred embodiment of the diluting substrate feed system (5) shown in FIG. 2, the diluting substrate feed system (5) comprises a substrate feed tank (8) in which substrate (X) may be stored as such or in a solvent solution. The diluting substrate feed system (5) also comprises a second filtration membrane (7). This second filtration membrane (7) is selected such that its permeability to the solvent (S) is higher than its permeability to the substrate (X). The permeability of the second filtration membrane (7) for the substrate (X) is selected such that the permeate P2 of the second membrane (7) contains the substrate (X) in a desired concentration in the solvent (S), such that it is suitable for being supplied to the reactor (2). The permeate side (21) of the second membrane (7) is connected to the reactor (2) for supplying permeate (P2) with the desired concentration of the substrate (X) in the solvent (S) to the reactor (2).

The second membrane (7) may be operated in a dead-end filtration mode, where the liquid permeating the membrane is supplied in a direction perpendicular to the membrane. The second membrane (7) is however preferably operated in a cross-flow filtration mode where the liquid permeating the membrane is supplied in a direction parallel to the membrane, as this ensures a sufficient degree of turbulence at the membrane surface.

The concentration of the substrate (X) in the substrate feed tank (8) is not critical to the invention and may be lower or higher, because the substrate concentration which is actually supplied to the reactor (2) will be determined by the second membrane (7). Often the substrate dilution in the feed tank may vary from 0.1-100 litre of solvent per mole of substrate, preferably 0.1-50 litre of solvent per mole of substrate, more preferably 0.5-25 litre of solvent per mole of substrate. Due to the relatively high, though not complete, rejection of the substrate X by the second membrane (7), substrate addition into the reactor (2) may occur at low substrate concentration, even when the substrate concentration in the feed tank (8) may be comparatively much higher. The second membrane (7) preferably has a substrate rejection of 50-99.5%, more preferably 60-95%. Substrate addition to the reactor may be further controlled by adapting the dosing rate, i.e. the flow rate of the diluted substrate-solvent mixture to the reactor. The latter may be adjusted and controlled through readily accessible operational parameters such as the transmembrane pressure and the temperature.

The retentate (20) of the second membrane (7) may be returned to the substrate feed tank (8) and may be supplied again to the second membrane (7) for supply to the reactor (2). According to an alternative embodiment, the retentate (20) may be replenished with substrate or solvent if necessary.

The first (6) and the second membrane (7) may have the same or different filtration characteristics. Usually however they will have different filtration properties, since the function of the first membrane (6) is to reject one or more of the substrate (X), reactant, reaction product (P), catalyst and any other compounds contained in the reaction mixture except for the solvent (S), whereas the function of the second membrane (7) is to permit permeation of a small, controlled amount of substrate (X).

Nevertheless the second membrane (7) may also function to reject one or more reactants to a desired extent, particularly in case the substrate feed tank (8) contains also one or more reactants besides the substrate.

The first (6) and second membrane (7) may be made of the same material, but usually they will be made of a different material.

A wide variety of materials is commercially available and may be selected by the skilled person taking into account the nature of the solvent, substrate, reactants and other components contained in the reaction mixture as described above.

The volume of the substrate feed tank (8) may vary within wide ranges, but usually its dimensions will be kept as small as possible taking into account the reactor volume, to minimize the solvent volume used. This embodiment of the diluting substrate feed system (5) allows to achieve substrate supply at low concentration, i.e. high dilution in solvent, to a reaction mixture, from a higher concentrated substrate feed solution with concomitant avoidance of problems associated with supply of droplets of highly concentrated substrate. Addition of substrate to a reactor at low concentration is particularly important for those reactions which, due to their inherent characteristics, must be carried out at low concentration in order to minimize the risk of unwanted impurities, such as for example cyclisation reactions used in the production of active pharmaceutical ingredients, in particular intramolecular macrocyclisation reactions, in which relatively small amounts of reaction product are produced in relatively large reaction vessels.

In a further embodiment of the diluting substrate feed system (15) shown in FIG. 1, the device used in the process of the present invention contains one single membrane, and the diluting substrate feed system (15) contains a mixing tank (19) for producing a substrate-solvent mixture with a desired substrate concentration. This embodiment also permits achieving the multiple goals of supplying substrate at low concentration to a reaction vessel from a high concentration feed solution and avoiding problems associated with the drop wise addition of a high concentration solution.

According to this embodiment, the diluting substrate feed system (15) comprises a substrate feed tank (18) to produce a desired dilution of the substrate (X) in the solvent (S). The substrate feed tank (18) may contain the substrate (X) as such, or it may contain a mixture of substrate (X) and solvent (S). The substrate feed tank (18) may further contain any other compound relevant to the reaction, for example one or more reactants, a catalyst, an initiator, etc. However, supply of these other reactive species may also occur separately from the substrate. Tank (18) will usually contain the substrate (X) in a relatively high concentration.

The diluting substrate feed system further comprises a mixing tank (19). This mixing tank (19) is connected to the substrate feed tank (18) permitting to send the concentrated substrate solution from the substrate feed tank (18) to the mixing tank (19). The mixing tank (19) is also connected to the permeate side (11) of the first membrane (6) to permit re-use of solvent from the reactor (2). Mixing of appropriate amounts of substrate (X) and solvent (S) permits producing a substrate/solvent mixture having the targeted concentration ratio. The substrate dilution in the substrate/solvent mixing tank (19) may vary within wide ranges, and will usually vary from 25 to 2500 litre of solvent per mole of substrate, preferably from 50 to 1000 litre of solvent per mole of substrate. The volume of the mixing tank (19) may vary within wide ranges, but usually its dimensions will be kept as small as possible taking into account the reactor volume, to avoid the use of too large solvent volumes.

The mixing tank (19) is connected to the reactor (2) via the reactor inlet (3). Thus a substrate/solvent mixture at a desired substrate concentration contained in the mixing tank (19) may be supplied to the reactor (2). Means may be provided to control the supply rate of the diluted solvent/substrate mixture to the reactor, for example the liquid flow rate may be controlled through operational membrane filtration parameters such as the transmembrane pressure and temperature. The solvent/substrate ratio within the mixing tank (19) may vary within wide ranges and will be selected by the skilled person taking into account the nature of the process involved, the risk of occurrence of unwanted side reactions in the reaction vessel and so on.

The device of the present invention may be designed such as to permit the controlled addition to the mixing tank (19) of other components than the substrate only.

The device used in the process of the present invention may also be conceived to comprise a dilution substrate feed system (5) as shown in FIG. 2, in combination with a dilution substrate feed system (15) shown in FIG. 1. According to another embodiment, the device of the present invention may comprise a diluting substrate feed system (5) as shown in FIG. 2 for supplying a first substrate to the reactor, and a dilution substrate feed system (15) shown in FIG. 1 for supplying a second substrate to the reactor. According to still another embodiment, the device of the present invention may comprise a plurality and/or a combination of diluting substrate feed systems as shown in FIG. 1 or 2 for supplying a first substrate to the reactor.

Using the device of the present invention, a chemical reaction may be carried out as follows.

In the embodiment shown in FIG. 1, dilution of the substrate (X) in the solvent (S) to a desired degree is obtained by supplying a concentrated substrate solution from a substrate feed tank (18) to a mixing tank (19) and mixing the substrate (X) with an appropriate amount of solvent (S). Substrate (X) thus diluted in solvent (S) is supplied to reactor (2) at an appropriate flow rate through reactor inlet (3), and is left to react with any other reactants and/or catalyst contained in the reactor (2). Simultaneously, through the outlet (4) of the reactor (2), reaction medium is withdrawn at an appropriate flow rate and conducted towards a first filtration membrane (6) and subjected to membrane filtration. This first membrane is permeable to the solvent (S) and impermeable to the substrate (X). Solvent (S) permeating the first membrane (6) is returned to the diluting substrate feed system (15), to provide dilution of the substrate (X) in the diluting substrate feed system (15). The retentate (10) of the first filtration membrane (6) containing substrate (X) which has not reacted, reaction product (P), catalyst and other reactants, is returned to the reactor (2). The procedure described above may be repeated until all substrate (X) has reacted. According to another embodiment, means may be provided to replenish the substrate (X), and reaction product (P) may be isolated from the reaction mixture as it is produced.

According to the embodiment of FIG. 2, appropriate dilution of the substrate (X) in the solvent (S) is obtained by supplying a concentrated substrate/solvent mixture contained in a substrate feed tank (8), to a second filtration membrane (7) which has a permeability for the solvent (S) that is higher than the permeability for the substrate (X). Thereby, the second membrane (7) will preferably be selected such that the permeate P2 of the second membrane (7) has the desired concentration of the substrate (X). The thus obtained permeate P2 of the second filtration membrane (7) is supplied to the reactor (2) at an appropriate flow rate along reactor inlet (3), and left to react with any other reactants and/or catalyst contained in the reactor (2). Simultaneously, along the outlet (4) of the reactor (2), reaction medium is withdrawn at an appropriate flow rate and conducted towards a first filtration membrane (6) and subjected to membrane filtration. Solvent permeating the first membrane (6) may be returned to the diluting substrate feed system (5), more specifically to the substrate feed tank (8) to provide dilution of the substrate (X) in the diluting substrate feed system (5). The retentate (10) of the first filtration membrane (6) containing substrate (X) which has not reacted, reaction product, catalyst and other reactants, is returned to the reactor (2), to have the residual substrate available for reaction. At the start of the process, the reactor (2) will usually contain a high concentration of reactants which are caused to react with the substrate (X), the substrate being supplied to the reactor (2) in a controlled concentration through membrane (7) or mixer (19).

The device used by the process of the present invention shows several advantages. The modular construction facilitates scaling up. An improved mass transfer may be guaranteed in comparison to prior art devices, and therefore the device may be of particular interest for use with processes wherein unwanted side reactions occurring with high substrate concentrations are to be avoided, where a risk exists to precipitation or poisoning of the substrate, to ensure that the substrate reacts as completely as possible, in reactions where the molecular weight of a polymer may be controlled by controlling the monomer:initiator ratio and intermolecular reactions of the monomer are to be avoided.

As a consequence of the membrane controlled supply of substrate into the reactor, and the separation and recycling of solvent from the mixture within the reaction vessel, the product yield may be substantially increased in comparison to standard high dilution reaction conditions presently used in industry.

The present invention is further illustrated in the examples below.

EXAMPLES

Example 1

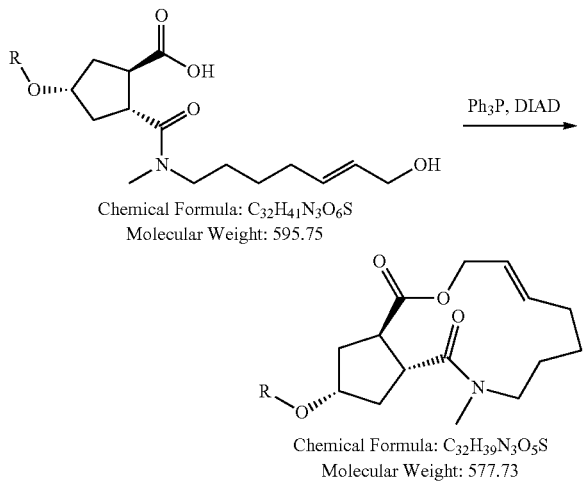

Scheme 1

The reaction shown in Scheme 1 is a model Mitsunobu lactonization to form a 13-membered ring.

The ring open precursor to cyclisation had a molecular mass of 595.75 g/mol and the lactone product had a molecular mass of 577.73 g/mole. A chemically cross-linked polyimide membrane (DuraMem™-200, Evonik-MET UK) was used to perform the in-situ solvent recovery (first membrane 6). The rejection of the substrate and product were both 99% and the reagents used to perform the Mitsunobu lactonization had a rejection of 99%.

The reaction was carried out as follows, using the equipment shown in FIG. 1. To a solution of triphenylphosphine (10.7 g) in dichloromethane (272 ml) under an atmosphere of nitrogen and cooled to 0° C. was added drop wise diisopropylazodicarboxylate (DIAD, 8.25 g) and the resulting mixture was stirred at 0° C. for 30 minutes. This solution was then added to the filtration loop feed tank, featuring in this experiment as reactor (2). The loop had been fitted with a filtration cell containing a pre-conditioned membrane.

The solution in the filtration loop was subjected to constant volume diafiltration using a solution of lactonization starting material (595 mg) dissolved in dichloromethane (500 ml) in mixing tank (19). The concentration of the starting material in mixing tank (19) was therefore 2 mmolar (500 l/mol). Permeate was recycled into mixing tank (19) and, in order to maintain the concentration of the diafiltration solution, to this was added concentrated lactonization starting material from feed tank (18), at such a rate that the concentration of the solution in mixing tank 19 remained constant. In this example, the feed tank (18) was filled with lactonization starting material (2.7 g) dissolved in dichloromethane (112 ml), i.e. a concentration of 40.5 mmolar (25 l/mol). On completion of the addition of the concentrated starting material solution in feed tank (18) to the solution in mixing tank 19, the diafiltration was continued until a minimum of 3 diafiltration volumes (starting volume in the filtration loop) had been added.

The conversion (100%) was determined by UPLC. Product yield was 74%, comparable to the yield of a batch reaction run at a concentration of 2 mmolar (500 l/mol).

Example 2

The same reaction was carried out as follows, using the equipment shown in FIG. 1. To a solution of triphenylphosphine (10.7 g) in dichloromethane (272 ml) under an atmosphere of nitrogen and cooled to 0° C. was added drop wise diisopropylazodicarboxylate (DIAD, 8.25 g) and the resulting mixture was stirred at 0° C. for 30 minutes. This solution was then added to the filtration loop feed tank featuring here as the reactor (2). The loop had been fitted with a filtration cell containing a pre-conditioned DuraMem™ 200 membrane.

The solution in the filtration loop was subjected to constant volume diafiltration using a solution of lactonization starting material (1.49 g) dissolved in dichloromethane (500 ml) in mixing tank (19). The concentration of the starting material in mixing tank (19) was therefore 5 mmolar (200 l/mol). Permeate was recycled into mixing tank (19) and, in order to maintain the concentration of the diafiltration solution, to this was added concentrated lactonization starting material from feed tank (18) at such a rate that the concentration of the solution in mixing tank (19) remained constant. In this example, the feed tank (18) was filled with lactonization starting material (2.7 g) dissolved in dichloromethane (112 ml) i.e. a concentration of 40.5 mmolar (25 l/mol). On completion of the addition of the concentrated starting material solution in feed tank (18) to the solution in mixing tank (19), the diafiltration was continued until a minimum of 3 diafiltration volumes (starting volume in the filtration loop) had been added. The conversion (100%) was determined by UPLC. Product yield was 66%, comparable to the yield of a batch reaction run at a concentration of 5 mmolar (200 l/mol).

Example 3

The same model reaction was used to demonstrate the principle of this invention using a 0.9 nm $TiO_2$ ceramic membrane (Inopor, Germany) in the equipment shown in FIG. 1. The rejection of the reaction starting material and product were both ≥95% and the reagents used to perform the Mitsunobu lactonization had a rejection of ≥81%.

To a solution of triphenylphosphine (10.7 g) in dichloromethane (272 ml) under an atmosphere of nitrogen and cooled to 0° C. was added drop wise diisopropylazodicarboxylate (DIAD, 8.25 g) and the resulting mixture stirred at 0° C. for 30 minutes. This solution was then added to the filtration loop feed tank, featuring in this experiment again as reactor (2). The loop had been fitted with a dry membrane.

The solution in the filtration loop was subjected to constant volume diafiltration using a solution of lactonization starting material (595 mg) dissolved in dichloromethane (500 ml) in mixing tank (19). The concentration of the starting material in mixing tank (19) was therefore 2 mmolar (500 l/mol). Permeate was recycled into mixing tank (19) and, in order to maintain the concentration of the diafiltration solution, to this was added concentrated lactonization starting material from feed tank (18), at such a rate that the concentration of the solution in mixing tank 19 remained constant. In this example, the feed tank (18) was filled with lactonization starting material (2.7 g) dissolved in dichloromethane (112 ml) i.e. at a concentration of 40.5 mmolar (25 l/mol). On completion of the addition of the concentrated starting material solution in feed tank (18) to the solution in mixing tank (19), the diafiltration was continued until a minimum of 3 diafiltration volumes (starting volume in the filtration loop) had been added. The conversion (100%) was determined by UPLC. Product yield was 84%, comparable to the yield of a batch reaction run at a concentration of <2 mmolar (>500 l/mol)

Example 4

The same model reaction was used to demonstrate the principle of this invention using a polymeric membrane to allow controlled addition of substrate into a reaction vessel, according to FIG. 2. A chemically cross-linked polyimide membrane (DuraMem™-300, Evonik-MET UK) was used as the second membrane 7 to deliver a low concentration solution of reaction starting material into the reaction vessel from a high concentration solution in the feed tank (8) as shown in FIG. 2. The retention of the lactonization starting material was ≥79%. For the first membrane 6 a chemically cross-linked polyimide membrane (DuraMem™-200, Evonik-MET UK) was used.

A solution of lactonization starting material (2.4 g) in tetrahydrofuran (THF) (170 ml) i.e. at a concentration of 23.7 mmolar (42 l/mol) was added to the feed tank (8) and subjected to constant volume diafiltration, with THF as diafiltration solvent, over a second membrane 7 that had been pre-conditioned with tetrahydrofuran (THF). The permeate from this diafiltration was added directly to a suspension of the Mitsunobu lactonization reagent that had previously been prepared via drop wise addition of diisopropylazodicarboxylate (DIAD, 2.2 g) to a solution (at 0° C. under an atmosphere of nitrogen) of triphenylphosphine (2.9 g) in tetrahydrofuran (18.5 ml) which had then been allowed to stir at 0° C. for 30 minutes before being warmed to 22° C. Once a sufficient volume of solvent had been permeated into the reaction vessel (2), the contents of the reaction vessel were passed over the first membrane (6), and the permeate from this filtration was added to the feed tank 8. Results showed a conversion of 55% and a product yield 68%, comparable to the yield of a batch reaction run at a concentration of 5 mmolar (200 l/mol).

Example 5

The model reaction of scheme 1 was used to demonstrate the principle of this invention using a polymeric membrane to allow controlled addition of reaction starting material into a reaction vessel, according to FIG. 2. A chemically cross-linked polyimide membrane (DuraMem™-200, Evonik-MET UK) was used as the second membrane 7 to deliver a low concentration solution of reaction starting material into the reaction vessel from a high concentration solution in the feed tank (8). The retention of the lactonization starting material was ≥98%. In this example no solvent recycling was performed.

A solution of lactonization starting material (2.5 g) in tetrahydrofuran (THF) (170 ml) i.e. at a concentration of 24.7 mmolar (40 l/mol) was added to the feed tank (8) and subjected to constant volume diafiltration, with THF as diafiltration solvent, over the second membrane 7 which had been pre-conditioned with tetrahydrofuran (THF). The permeate from this diafiltration was added directly to a suspension of the Mitsunobu lactonization reagent which had previously been prepared via drop wise addition of diisopropylazodicarboxylate (DIAD, 22 g) to a solution (at 0° C. under an atmosphere of nitrogen) of triphenylphosphine (29 g) in tetrahydrofuran (42 ml) which had then been allowed to stir at 0° C. for 30 minutes before being warmed to 22° C. Results: conversion of 100% and yield of 95%, comparable to a batch reaction which was run at infinitesimally low concentration.

Example 6

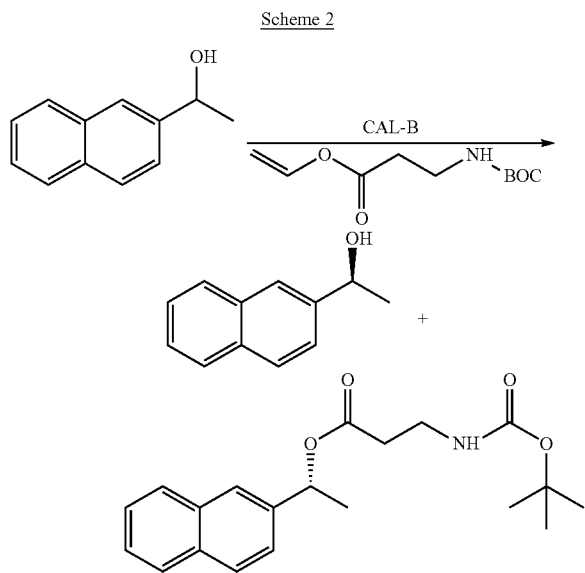

The reaction shown in scheme 2 is a model biocatalyzed kinetic resolution based on the procedure published by M. Brossat et. al. in Org. Process Res. Dev. 13 (2009) 706-709, which was chosen to demonstrate the principle of this invention using the configuration as shown in FIG. 2 and as first membrane 6 a 5 nm TiO$_2$ ceramic membrane (Inopor, Germany). The retention of the lipase *Candida antartica* lipase B (CAL-B) was designed to be ≥99% and this of the reagents, starting materials and reaction product was <20%. The second membrane 7 consisted of a 0.9 nm TiO$_2$ ceramic membrane (Inopor, Germany). The retention of the reaction starting material and of the acyl donor was designed to be <50% and of the product being ≥75%. Product inhibition of the enzyme is avoided because the concentration of acylated alcohol product in the solution of alcohol starting material is maintained at low concentration within the reactor.

Example 7

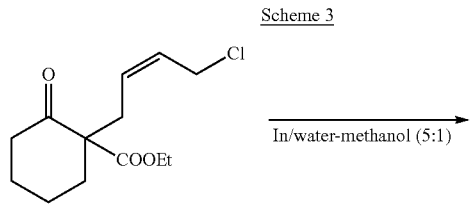

-continued

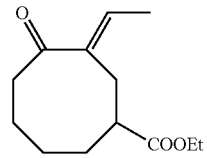

A model carbocyclic ring expansion via a barbier type reaction similar to that published by Li et. al. Tetrahedron 54 (1998) 2347, has been selected to demonstrate the principle of FIG. 1 using as first membrane 6 a Dow Filmtech BW membrane. The retention of all reaction components besides the aqueous solvent was designed to be 99%.

The reaction was carried out as follows using the equipment shown in FIG. 1. Cyclohexanone starting material (3.10 g) was dissolved in 300 ml of a mixture of water (225 ml) and methanol (75 ml), the concentration of this solution was therefore 40 mmolar (25 l/mol). This solution was in this experiment entered into the feed tank (18). 37.5 ml of this solution was added to the mixing tank (19) and diluted to a volume of 300 ml with a water-methanol mixture having the same component ratio as used to prepare the previous solution. The concentration in the mixing tank (19) was therefore 5 mmolar (200 l/mol). To the filtration loop, featuring in this experiment as circulating over the reactor (2), was added 2.75 g of indium powder in 120 ml of a mixture of water (90 ml) and methanol (30 ml).

The mixture in the filtration loop was subjected to constant volume diafiltration using the solution in the mixing tank (19). Permeate (11) was recycled into the mixing tank (19) and in order to maintain the concentration of the diafiltration solution, to this was added concentrated cyclohexanone solution from the feed tank (18) at such a rate that the concentration of the diafiltration solution in mixing tank (19) remained constant. On completion of the addition of the concentrated starting material solution in feed tank (18) to the solution in mixing tank (19), the diafiltration was continued until a minimum of 3 diafiltration volumes had been added. The conversion (100%) was determined by GC. Product Yield was 70%.

The invention claimed is:
1. A process for carrying out a chemical reaction of a substrate (X) in a diluted reaction mixture comprising a solvent (S), the reaction being selected from a cyclisation reaction, a polymerization reaction, an enzymatic reaction showing substrate inhibition, an enzymatic reaction showing product inhibition, a reaction showing precipitation of the substrate or of the reactant, and combinations thereof, the process comprising the steps of
   a) supplying a diluted substrate-solvent mixture to the inlet (3) of a reactor (2),
   b) causing the substrate in the diluted reaction mixture in the reactor (2) to react,
   c) discharging, from an outlet (4) of the reactor (2), reaction mixture comprising reaction product, solvent, and substrate that has not reacted,
   d) conducting the reaction mixture to a first filtration membrane (6), with a retentate side (10) and a permeate side (11), whereby the first filtration membrane (6) is permeable to the solvent (S) and having a substrate (X) rejection of 80%-100%,
   e) returning retentate (R) comprising substrate (X) that has not reacted, from the retentate side (10) of the first filtration membrane (6) to the reactor (2), wherein in step (a) said diluted substrate-solvent mixture is supplied to said inlet of said reactor from a diluting substrate feed system (5, 15) comprising an outlet connected to the inlet (3) of the reactor (2); wherein the diluting substrate feed system (5) for supplying substrate to the reactor (2) comprises a second filtration membrane (7) which is permeable to the solvent (S), wherein the permeability of the second filtration membrane (7) for the substrate (X) is selected such that the permeate (P2) of the second membrane has a concentration of the substrate (X) in the solvent (S), wherein permeate (P2) with the concentration of the substrate (X) in the solvent (S) is supplied from the permeate side (21) of the second filtration membrane (7) to the reactor (2);

further comprising the step of returning solvent (S) which permeated the first filtration membrane (6) from the permeate side (11) of the first membrane (6) to said diluting substrate feed system (5, 15) to dilute the substrate in the diluting substrate feed system (5,15) thereby forming said diluted substrate-solvent mixture; and supplying a concentrated substrate solution from a substrate feed tank (18) to a mixing tank (19) in the diluting substrate feed system (5).

2. The process according to claim 1, wherein the first filtration membrane (6) has a rejection of at least one compound selected from the reaction product, catalyst and one or more of the reactants which are caused to react with the substrate of 60-95%, and wherein the at least one compound is returned from the retentate side (10) of the first filtration membrane (6) to the reactor (2).

3. The process according claim 1, wherein the first membrane (6) has a substrate rejection of at least 95%.

4. The process according to claim 1, wherein the second filtration membrane (7) comprises a retentate side (20), and substrate (X) which is rejected by the second filtration membrane (7) is supplied to the substrate feed tank (8) and is further mixed with solvent, and wherein a mixture containing solvent and substrate is supplied from the substrate feed tank (8) to the second filtration membrane (7).

5. The process according to claim 4, comprising the returning of solvent (S) from the permeate side (11) of the first filtration membrane (6) to the substrate feed tank (8) with the purpose of replacing solvent which has been supplied to the second membrane (7).

6. The process according to claim 1, wherein the second filtration membrane (7) has a substrate rejection of 50%-99.5%.

7. The process according to claim 1, wherein the first and second filtration membranes (6, 7) are different.

8. The process according to claim 1, wherein the first and second filtration membrane (6, 7) have the same performance characteristics.

9. The process according to claim 1, wherein the first and second filtration membrane (6, 7) are independently selected from the group consisting of a nano-filtration membrane, a microfiltration membrane, an ultrafiltration membrane, a reverse osmosis filtration membrane, and combinations thereof.

10. The process according to claim 9, wherein at least one of the first and second filtration membrane (6, 7) are nanofiltration membranes.

11. The process according to claim 1, wherein the mixing tank (19) comprises a solvent/substrate mixture with a substrate dilution of 50-1000 liter of solvent per mole of substrate.

12. The process according to claim 1, further comprising conducting solvent (S) containing permeate from the permeate side (11) of the first filtration membrane (6) to the mixing tank and mixing the permeate with substrate supplied from the substrate feed tank (18) to the mixing tank (19), and supplying the substrate-solvent mixture from the mixing tank (19) to the reactor (2).

13. The process according to claim 1, wherein the substrate in the substrate feed tank (8, 18) of the diluting substrate feed system (5) has a substrate dilution of 0.5-25 liter of solvent per mole of substrate.

14. The process according claim 1, wherein the substrate dilution at the reactor inlet (3) is 50-1000 l/mol.

15. The process according to claim 1, wherein at least one of the group consisting of the first membrane (6), the second membrane (7), and both the first and the second membrane (6, 7), is operated in cross-flow.

16. The process according to claim 1, wherein the substrate is a compound which is capable of undergoing at least one chemical reaction selected from an intramolecular reaction and a homo- or hetero-intermolecular reaction.

17. The process according to claim 1, wherein the substrate is an organic compound.

18. The process according to claim 1, wherein the substrate feed is supplied continuously or intermittently in portions.

19. The process according to claim 1, wherein the reactor (2) contains at least 100 liter of reaction medium per mole of substrate.

20. The process according to claim 10, wherein the membranes are solvent resistant nanofiltration membranes.

* * * * *